(12) United States Patent
Jones et al.

(10) Patent No.: US 7,084,980 B2
(45) Date of Patent: Aug. 1, 2006

(54) SPR INTERFEROMETER

(75) Inventors: Robert Jones, Cambridge (GB);
Michael Hazel, Cambridge (GB);
Gavin Roberts, Colchester (GB)

(73) Assignee: Cambridge Consultants Limited,
Cambridge (GB)

( * ) Notice: Subject to any disclaimer, the term of this patent is extended or adjusted under 35 U.S.C. 154(b) by 0 days.

(21) Appl. No.: 10/485,716

(22) PCT Filed: Aug. 1, 2002

(86) PCT No.: PCT/GB02/03543

§ 371 (c)(1),
(2), (4) Date: Oct. 22, 2004

(87) PCT Pub. No.: WO03/014715

PCT Pub. Date: Feb. 20, 2003

(65) Prior Publication Data

US 2005/0052655 A1     Mar. 10, 2005

(30) Foreign Application Priority Data

Aug. 6, 2001    (GB) ................................ 0119062.8

(51) Int. Cl.
*G01N 21/55*    (2006.01)

(52) U.S. Cl. ...................... 356/445; 356/495; 356/491
(58) Field of Classification Search ................ 356/495, 356/491, 450
See application file for complete search history.

(56) References Cited

U.S. PATENT DOCUMENTS 5,485,277 A * 1/1996 Foster ........................ 356/445
5,999,262 A   12/1999 Dobschal et al.

FOREIGN PATENT DOCUMENTS

| DE | 198 14 811 C 1 | 8/1999 |
| WO | WO 93/14392 | 7/1993 |
| WO | WO 95/22754 | 8/1995 |
| WO | WO 01/20295 A2 | 3/2001 |

OTHER PUBLICATIONS

S.G. Nelson, et al. "High sensitivity surface plasmon resonance sensor based on phase detection." Sensors and Actuators B, Elsevier Sequoia Science S.A., Lausanne, CH, vol. 35, No. 1, Sep. 1, 1996, pp. 187-191, XP004049753, ISSN: 0925-4005.

* cited by examiner

*Primary Examiner*—Gregory Toatley
*Assistant Examiner*—Marissa J Detschel
(74) *Attorney, Agent, or Firm*—Blakely, Sokoloff, Taylor & Zafman; Stephen M. De Klerk

(57) ABSTRACT

The present invention concerns an interferometer comprising: an optical body adapted in operation to mount a measurement area comprising a film which is capable of acting as a two dimensional environment for surface plasmons and an adjacent reference area; an optical beam generation means for irradiating the reference and measurement areas with radiation capable of generating surface plasmon resonance; optical means for combining radiation reflected from the reference and measurement areas, and pixelated detection means for generating data representing two dimensional images of the combined radiation beams.

22 Claims, 17 Drawing Sheets

SPR INTERFEROMETER

This Application is a National Phase of International Application No. PCT/GB02/03543 filed on Aug. 1, 2002, which claims priority from Great Britain Patent Application No. 0119062.8, filed on Aug. 1, 2001.

BACKGROUND OF THE INVENTION

1. Field of the Invention

The present invention relates to optical interferometers. Interferometers are used in many fields but the present invention is particularly, though not exclusively, concerned with interferometers whose applications include the detection of optical phase changes due to surface binding under surface plasmon resonance (SPR) conditions and to the detection of binding at multiple, discrete sites in the surface using the phase images thereby obtained.

2. Description of the Related Art

Surface Plasmons (SP) are collective oscillations of free electrons constrained to move in a thin film of a conductor considered as a two-dimensional environment. These oscillations are excited by external electromagnetic radiation coming from a high refractive index medium. For a given configuration there exist a relatively small range of film thickness for which resonance is supported. Film thickness outside of this range are non-resonant. Surface plasmons also have a characteristic propagation length that limits fundamentally the spatial resolution achievable with this technique.

SPR is used in molecular binding detection analysis where typically molecules to be tested are deposited on the thin film and potential binding agents are passed in a solution or gas over the rear face of the thin film. If binding occurs between a molecule and a binding agent under SPR conditions the refractive index at that point will change and can be detected.

Uses of molecular binding detection analysis include, but are not limited to, measuring the expression levels of genes and proteins in biological samples, determining the functions of genes and proteins, identifying actual or potential therapeutic drugs and other molecules, determining the biological effects of actual or potential therapeutic drugs and other molecules. These applications can be used in biological research activities, in discovery and development of drugs, and as diagnostic tests.

In prior art a Mach Zehnder device has been configured to measure SPR phase changes produced by variations in the refractive index of a gas local to the measurement surface. A major disadvantage of this type of device, particularly with respect to routine laboratory use, is that it requires four independent components: two beam splitters and two mirrors, one of which is the resonant surface in the case of the SPR configuration. As a result, the arrangement is relatively bulky and, more critically, the output is sensitive to sub-wavelength relative displacements of these components and hence very small mechanical and environmental perturbations.

BRIEF DESCRIPTION OF THE DRAWINGS

In order that the present invention may be more clearly understood, embodiments will now be described by way of example and with reference to the accompanying drawings, in which.

DETAILED DESCRIPTION OF THE INVENTION

Figure 1:
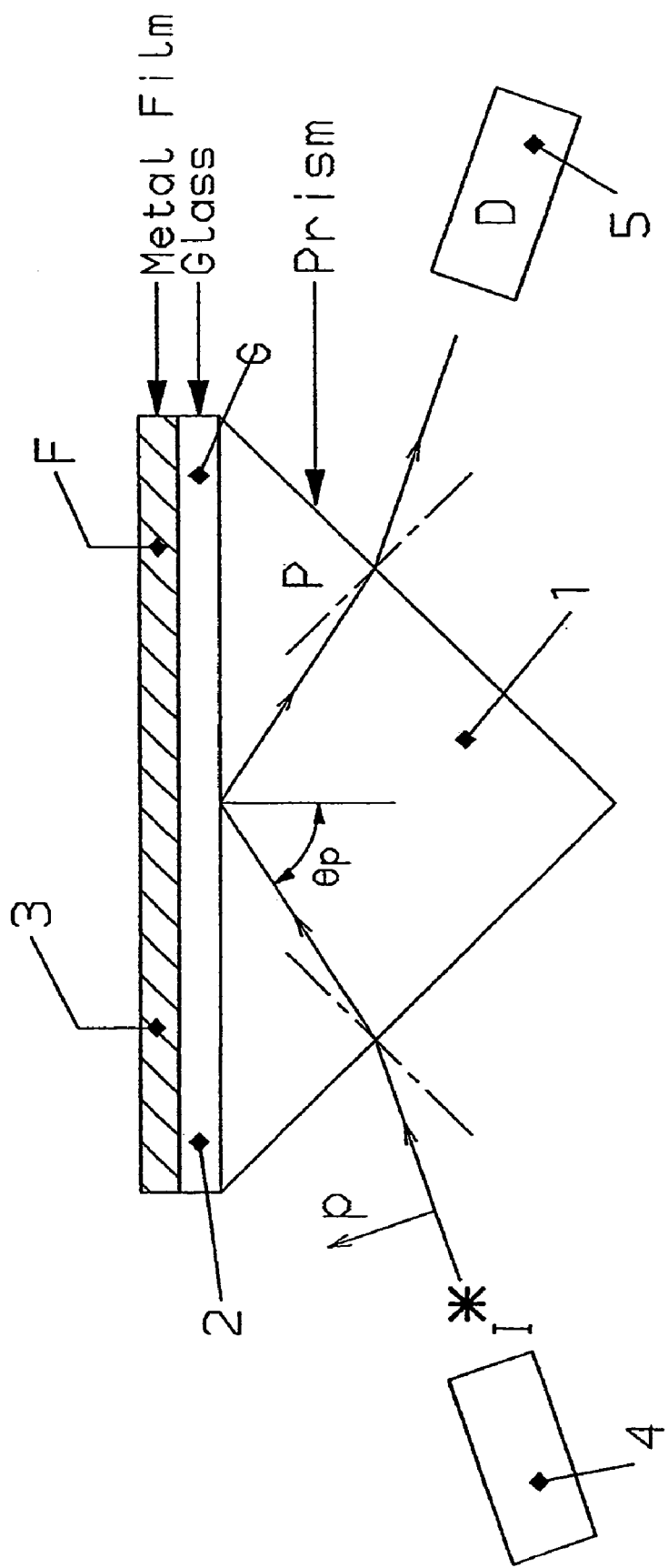
FIG. 1 is a diagrammatic cross section through the known (Kretschmann) configuration of optics for illuminating a surface under SPR conditions.

Before the embodiments of the invention shown in the drawings are described there will be given a brief resume of the basic principles of SPR with regard to the known Kretschmann configuration shown in FIG. 1. This comprises a prism 1, a slide in the form of an optical flat glass plate 2 optically contacted to the base of the prism 1 and a thin metallic film 3. Normally the film 3 is coated with a chemical layer 3' to which are bound molecule ligands. The chemical layer may, for example, consist of carboxymethyl dextran and typical probe molecules include antibodies, enzymes and proteins. The angle of the prism 1 depends upon its refractive index that of the optical flat and the medium in contact with it. For the high refractive index glass required for resonance in contact with water it is typically 60°. The film 3, can for example, be of gold or silver and has a thickness in the range typically 20 nm to 50 nm depending on the sharpness of the resonance i.e. the angular width $\theta_r$ required. The metal film 3 acts as a two dimensional environment for surface plasmons (SP). These are, as already mentioned, the collective oscillations of free electrons which are confined to move in the film and which are excited into oscillation by external electromagnetic radiation coming from the high refractive index medium provided by the prism 1 and the optical flat 2. The radiation is in the form of an input beam of polarised light from a suitable light source 4. To maximise the resonant component of the reflected light the light beam is polarised in the plane of incidence. (i.e. it is p polarised). The output light field is converted to an electronic signal by a suitable opto-electronic detector 5 and output data is generated from output electronic signal by appropriate circuitry connected to the detector (i.e. 6 as shown in a specific implementation in FIG. 3).

Figure 2:
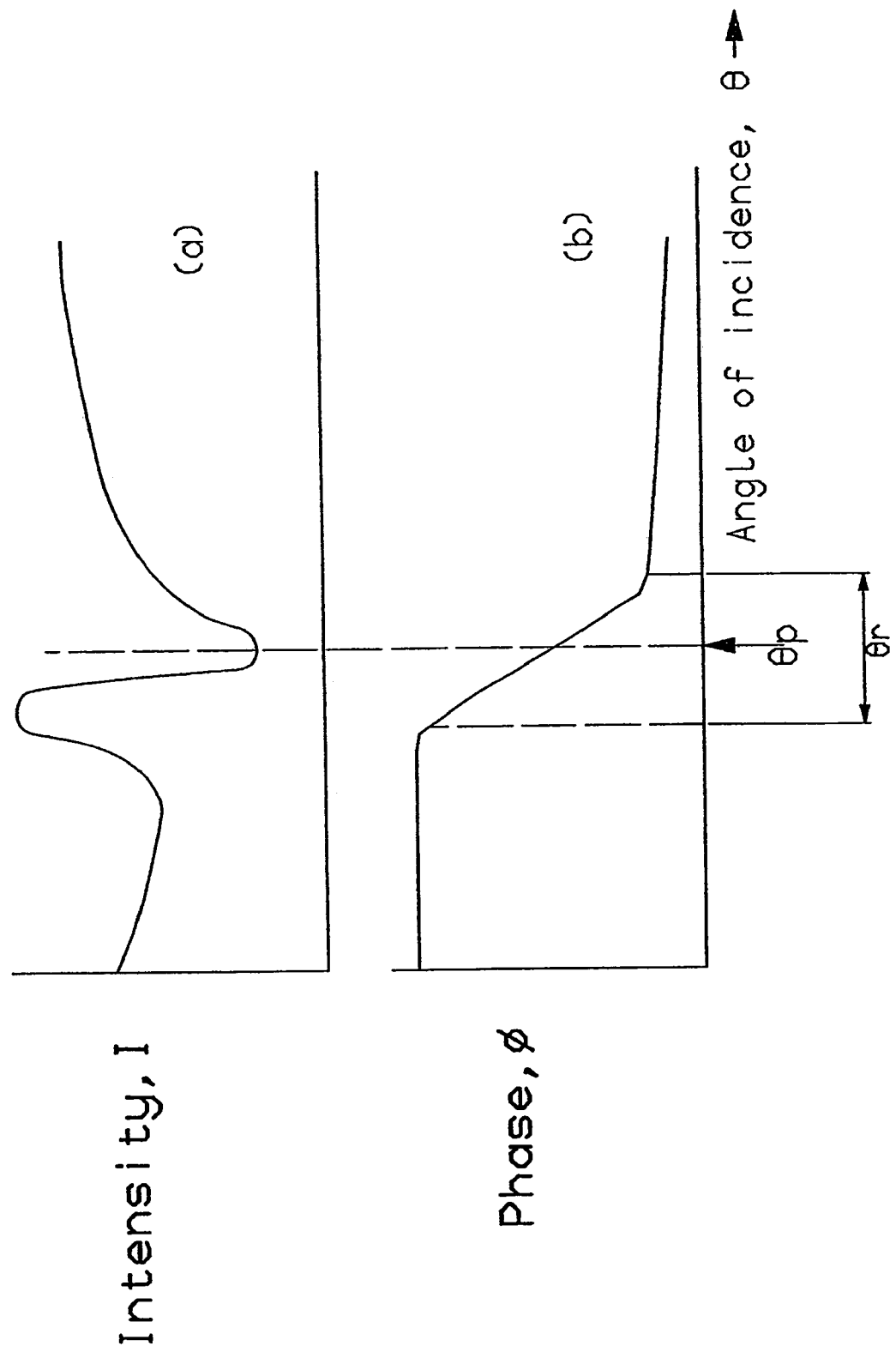
FIG. 2 shows a graph illustrating the non-linear resonant characteristics in the intensity (I) and phase domain ($\phi$) of the light reflected from the surface in FIG. 1 over the range for which surface plasmons are generated.

FIG. 2 shows the variation in the intensity and the phase of the light reflected from the surface in FIG. 1 over the angular resonant range $\theta_r$ for which resonant surface plasmons are generated. The angular position of the resonant intensity minimum $\theta_p$ for a given film material is a sensitive function of the refractive index of the medium in direct proximity with the surface. Changes to molecules bound to the surfaces due to interaction and binding with other modules affect the local refractive index and therefore modulate the position of minimum shown in FIG. 2.

Existing systems of this type operate predominately in the intensity domain. In one such approach the co-ordinate of the intensity minimum is determined from that of the corresponding dark line that is observed when a divergent light field is incident on the resonant surface and it is imaged by the detector (1). Differential imaging techniques using plane wave illumination in which images recorded before and after resonant shift are subtracted to display local change have also been used. The former of these methods can not be easily adapted to measure small areas and the resolution of the latter is limited by image noise and optical power throughput. This constrains the extent to which they can be used to image and measure multiple, small binding sites.

The present invention is concerned with avoiding the limitations of these known methods and involves Phase domain $\phi$ imaging. The reason for this is that the phase $\phi$ varies approximately linearly with respect to the resonant angle $\theta_r$ and hence a small angular shift of the resonance $\Delta\theta_p$ causes a phase shift $\Delta\theta$ where:

$$\Delta\phi = \frac{d\phi}{d\theta_r}\Delta\theta_p \quad (1)$$

and $$\left(\frac{d\phi}{d\theta_r}\right) =$$

variation of phase with respect to angle over the resonant region

The measurement of $\Delta\phi$ requires that the arrangement shown in FIG. 1 be incorporated in an interferometer such that the wavefront reflected from the resonant surface interferes with a reference wavefront. The fringe shift in the resultant interference pattern due to changes in local refractive index as the result, for example, of molecular binding can then be detected.

The embodiments of the invention to be described hereinafter have as a principle concern the reduction of the noise due to mechanical and thermal perturbations to a minimum to thereby enable maximum measurement sensitivity to be achieved (i.e. as limited fundamentally by the source and detector noise and the plasmon propagation length).

Figure 3:
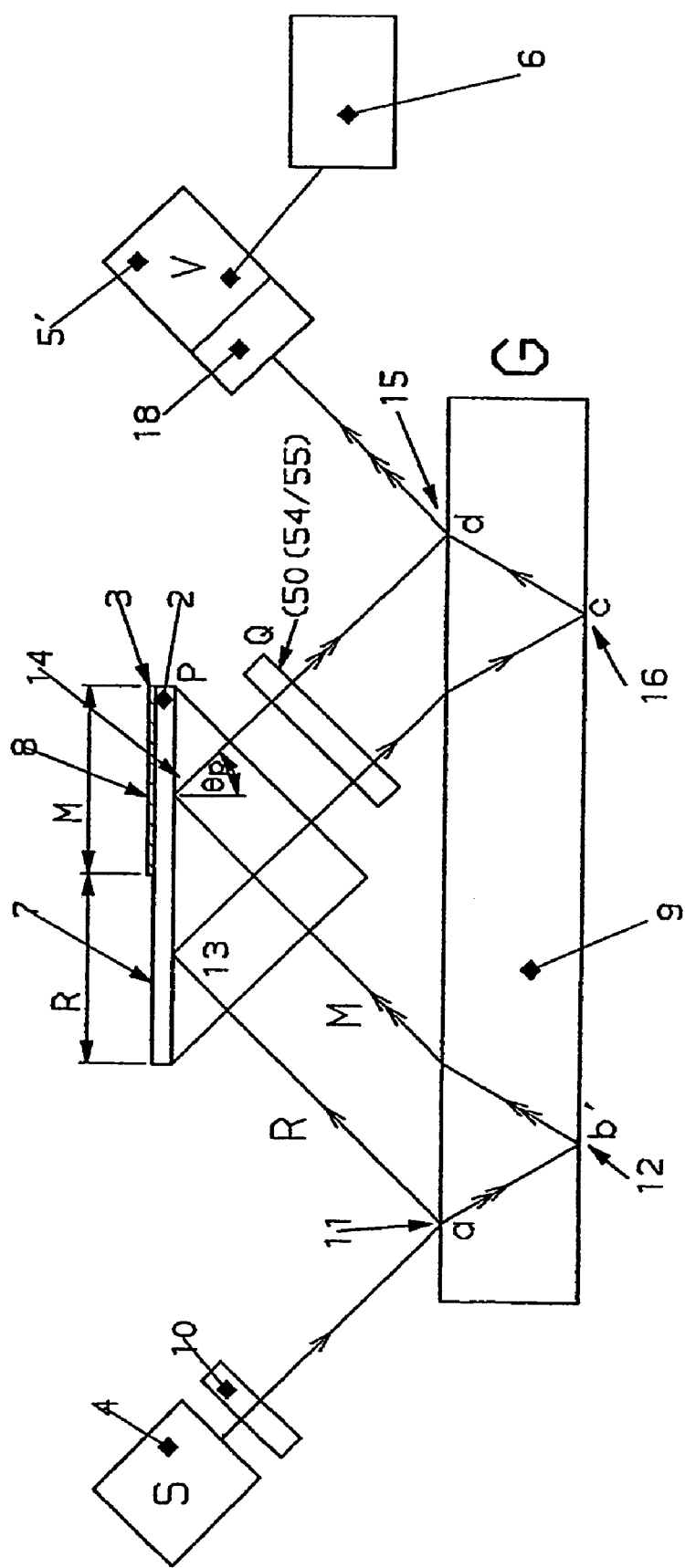
FIG. 3 is a diagram showing the basic configuration of an interferometer in an embodiment in accordance with the present invention.

Turning now to the basic geometry of the interferometer that is the subject of the present invention shown in FIG. 3, it will be seen that this embodiment incorporates the same basic configuration of prism 1, optical flat 2, polarised light source 4, a photosensitive detector and electronic circuitry 6. However in this embodiment the detector 5' is pixelated so that it can generate two dimensional images for subsequent recording and display. Thus as will be described hereinafter with regard to FIG. 15 the signal processing circuitry 6 also has to operate in a manner different from the prior art configuration.

However, it will be seen that the film 3 covering the base face of the prism is varied so that the base face is divided with two areas 7 and 8. Area 7 is treated so as to be non-resonant and thereby provide a reference area. This can be achieved by increasing the thickness of this film area to a non-resonant value. Area 8 is the measurement area and is created in a manner similar to the film of the prior art SPR configuration in FIG. 1.

In an alternative configuration of particular relevance to the detection of molecular binding, the reference and measurement regions have the same resonant thickness but with only the measurement region being coated with a suitable molecular binding coating. In both cases the differential phase is proportional to the binding that occurs when a buffer fluid or analyte containing the binding molecules is flowed simultaneously over the reference and measurement surfaces.

The embodiment of FIG. 3 has additional components in the form of a parallel faced optical flat 9 in the path of the beam of light from the polarised light source 4 and beam shaping optics 10. The beam shaping optics 10 will be described in greater detail hereinafter. The optical flat 9 is mounted normally parallel to the base of prism 1.

The detector 5' of this embodiment is pixelated so as to generate an image of the combined beam reflected from the respective reference and measurement areas. Fourier Transform and Phase Stepping techniques may be conveniently used to measure the relative phase of the reference and measurement beam as a function of pixel co-ordinate in the 2D array and are described later. Under SPR conditions the local phase changes will correspond to those induced by changes in the refractive index at the surface due, for example, to molecular binding. This mode of operation requires that the illumination and viewing optics of the specific forms discussed later be used. A 2D phase image of the SPR binding is thereby generated. In a particular configuration the measurement surface may be patterned with an array of discrete sites each having different binding properties (e.g. ligands) and the response to a given molecule (e.g. a specific protein) determined from the previously described phase image.

In operation a beam of light from the source 4 and optics 10 is partially reflected from the front face of the optical flat 9 at a point 11 to form a reference beam R and the transmitted beam is reflected from the rear face of optical flat 9 at 12 to form a measurement beam M. The beams R and M are incident on the areas 7 and 8 respectively at points 13 and 14. The reference and measurement beams R and M recombine at point 15 by being reflected from the rear face of optical flat 9 at 16 and the front face of optical flat 9 at point 15. The measurement beam M generates surface plasmon resonance at point 14 but, depending on the arrangement used, either no resonance or binding refractive index change is generated at point 13. The combined beam is incident on the pixelated detector 5' via viewing optics 18 so as to generate an image which is analysed by the circuitry shown at 6. An additional optical element 50 may be incorporated in the interferometer to modify the relative phase of the reference and measurement beam in accordance with the requirements of the phase measurement technique.

Figure 4:
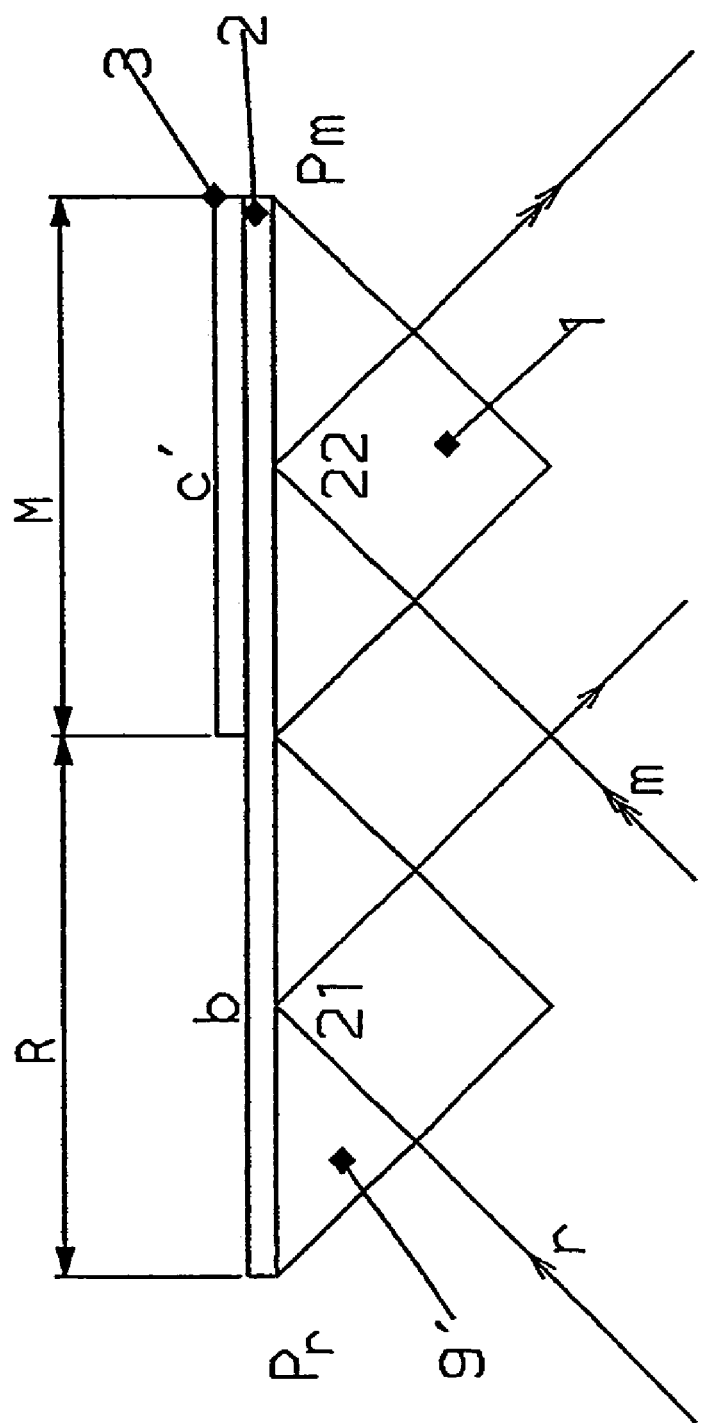
FIG. 4 is a diagram showing part of a second embodiment of the present invention.

FIG. 4 shows a second embodiment which in principle operates in exactly the same manner as the first embodiment. However in the second embodiment there is provided an additional prism 9' similar to prism 1 but which acts as a reference prism as the base of this second prism is treated in a manner similar to reference area 7 so as to be non-resonant. In this embodiment a plane polarised reference light beam from a light source 4 impinges on prism 9' to be reflected at point 21 to form a reference beam R and the measurement beam from source 4 impinges on prism 1 to be reflected at point 22 so as to generate surface plasmon resonance and to provide as before a measurement beam M. As in the previous embodiment the reference and measurement beams will generate a two dimensional image on the pixelated detector 5'. Thus the phase of the resonant measurement beams is measured as a function of the spatial co-ordinates as detected by the pixelated detector array 5' and can be used by the processing circuitry 6, as the previous embodiment, to establish an image of binding events over an array of discrete binding sites 8 in the measurement areas.

The stability of the two embodiments described above results from the commonality of the beam division/recombination and reference/measurement optical elements. Spatially uniform relative displacements of these components have a common effect on the path lengths of the reference and measurement beams and accordingly do not cause relative phase shifts. A relative rotation of the components generates a spatially uniform phase change which may be subtracted when detecting localised phase variations. A further advantage of the preferred configurations is that any phase shifts not associated with resonant binding that are common to the surface that embodies the reference and measurement zones cancel out automatically.

There will now be discussed the criteria defining the input illumination and output imaging optics of the interferometer shown in FIGS. 3 and 4 in order for them to be compatible with the phase imaging discussed above.

The first requirement is that the angular divergence $\beta$ of the illumination light field has to be small with respect to the angular width of the resonance $\theta_r$ in order to minimise the convolutive blurring of $\phi$ with respect to $\theta$ and the resultant loss of sensitivity $d\phi/d\theta$. It also has to be spectrally narrow band in order to prevent equivalent blurring in the spectral domain.

In the general case the requirements for imaging are demanding. This is because the object plane (i.e. measurement surface) is inclined at a large angle (typically 60°) to the viewing direction and is observed through a varying depth of glass through the prism. It is noted however, that the composite reference and measurement surface is effectively a plane, internal mirror. The light reflected from individual elements of the measurement surface hence propagate as corresponding elements of the reflected wavefront. Under these conditions any lens used in the output path of the interferometer need only serve the significantly less demanding function of modifying the geometry of the interfering wavefronts.

Figure 5:
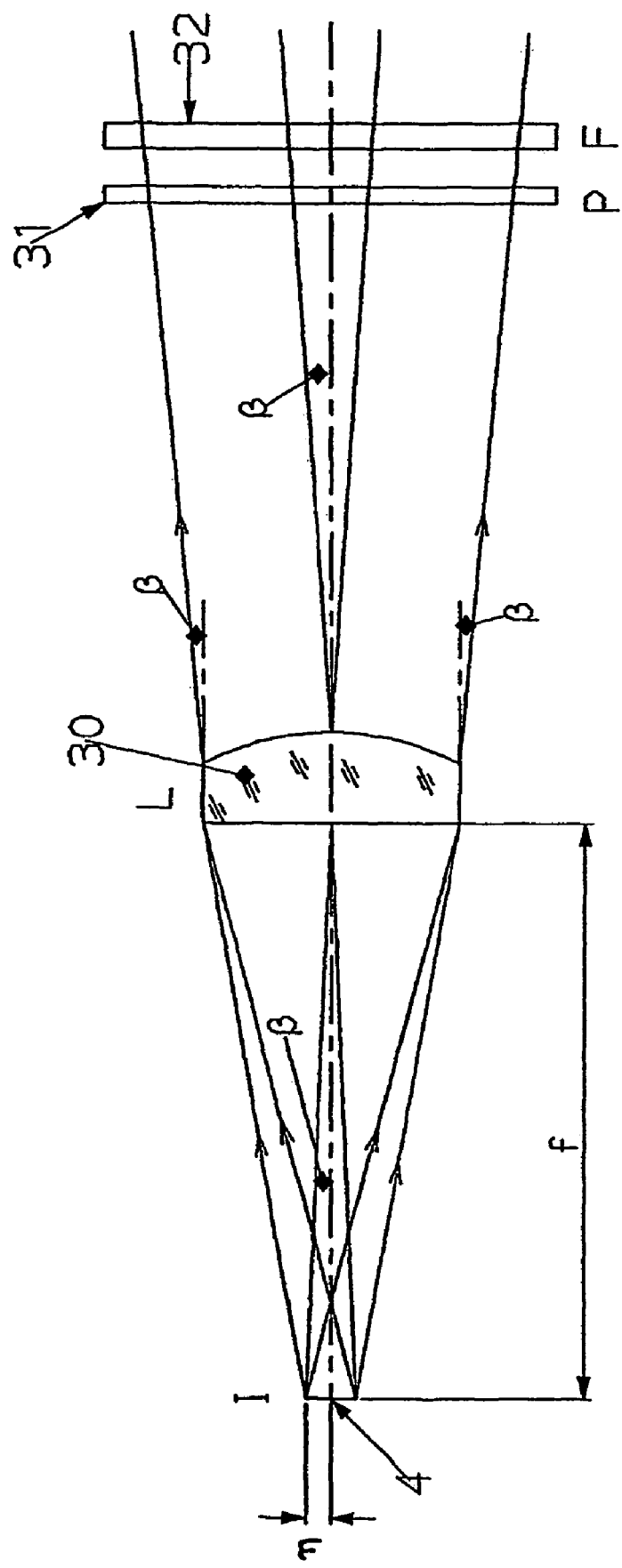
FIG. 5 is a diagram showing the collimation of an extended illumination source.

The above requirements are mutually compatible with the use of a collimated monochromatic 'point source' as shown in FIG. 5. Here the light from the source 4, of small, finite diameter $\eta$, is collimated by the lens 30 of focal length f. The divergence $\beta$ of the collimated wavefront is given by:

$$\beta = \eta/f \qquad (2)$$

$\beta$ is reduced to the minimum value by using a source with minimum radius $\eta$ and extending the focal length f of an optimal lens form to the maximum practical value. In practice the source may consist of:

(a) a pin-hole back illuminated by light focussed from a spectrally filtered, extended white light source ($\eta \sim 100$ μm);

(b) a single wavelength laser ($\eta \sim 1.5$ μm);

(c) a single mode fibre into which light the laser in (b) is coupled ($\eta \sim 5$ μm).

In the case of (a) it is noted that the filter (32) may follow the polariser (31) and collimating lens 30 as shown in FIG. 5.

In the limit that the sources size tends to $\lambda$ (the light wavelength) $\beta$ tends towards the diffraction limited values of $\lambda/f$ which fundamentally limits the degree of collimation. In practice this is closely approximated by (b) and (c) above.

Lasers (b), (c) are preferred to a white light source (a) because the optical power throughput of the latter is significantly less than the former due to the low coupling efficiency of light from the extended source through the small pin-hole and attenuation by the narrow pass band spectral filter (typical spectral width 10 nm). In addition minimum values of $\beta$ and hence convolutive resolution loss are attainable using a laser source. The general disadvantage of a laser for imaging applications is that the scatter and diffraction of laser light at random micro defects in the optical surfaces generates image noise. This is due to the high spatial and temporal coherence lengths Xc and Lc of the light field where, $$x_C = \frac{0.3 f \lambda}{\eta} \qquad 3(a)$$

$$L_c = \frac{\lambda^2}{\Delta\lambda} \qquad 3(b)$$

and, $\lambda$ = wavelength $\Delta\lambda$ = spectral width

Coherent noise impairs intensity domain images of SPR binding for which it has been found necessary to use the lower coherence pin-hole arrangement (a) with the attendant loss of optical power and image signal to noise ratio. By comparison phase domain processing is intrinsically less sensitive to such noise due to operation in either a narrow band of spatial frequency (Fourier Transform method) or an intensity independent mode (Phase Stepping method). These phase imaging techniques which will be discussed in detail herewith are consequently compatible with illumination derived from a laser source. The resultant increase in SNR due to the higher optical power throughput and the reduced image blur provides a route to optimal imaging.

There will now be discussed those aspects of interferometer design that are related to the specific requirements of the Fourier Transform and Phase Stepping techniques used in preferred embodiments of the invention for measuring the relative phase of the reference and measurement beams.

Firstly, the Fourier transform method will be discussed.

In this method a phase variation is introduced between the interfering wavefronts that varies linearly with respect to spatial co-ordinates. The intensity at a point in the resultant linear fringe pattern superimposed upon the detected image is given by, $$I(r)=a(r)+b(r).\sin(k.r) \quad (4)$$

which can also be expressed as complex exponentials, $$I(r)=a(r)+c(r).e^{i(k.r)}-c^{\pm}(r).e^{-i(k.r)} \quad (5)$$

where $$c(r)=0.5b(r)e^{i\phi(r)}$$

The 2-D Fourier transform of the intensity profile consists of a complex function that has three main local maxima of its absolute value. These occur one at the DC level, and two from the carrier frequency (i.e. one at $f_o$ and one at $-f_o$)

The 3-lobed function in frequency space is then translated such that the lobe at $f_o$ is moved to DC. An apodisation function is then applied so that the other lobes of the function are suppressed. In one implementation there can be used a Gaussian function centred at what was the carrier frequency, and whose $3\sigma$ point is at what was the DC point. The inverse Fourier transform is then taken of this data, which leaves only one term from the complex intensity expression above. Taking natural logs of the system, and noting that phase can be extracted from the polar form of complex expressions we find, $$\ln(z)=\ln(re^{i\theta})=\ln(r)+i\theta \quad (6)$$

Thus the phase can be extracted by taking only the imaginary part of the output of the inverse Fourier Transform.

Figure 6:
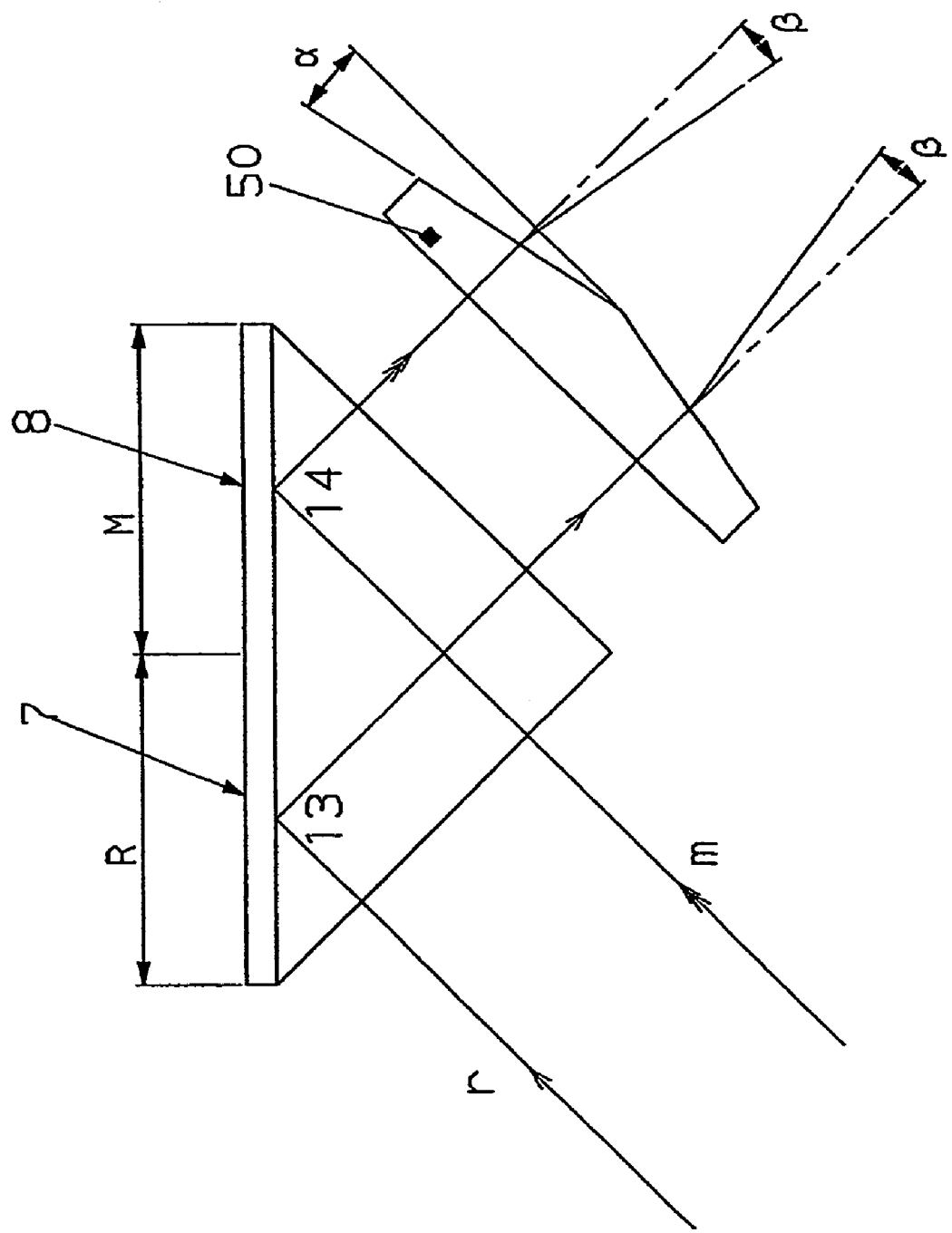
FIG. 6 is a diagram showing part of the interferometer in which a bi-prism is introduced to generate an angular shear between the interfering wavefronts.

The spacing of the fringe described by equations 4, 5 needs to be nominally 0.2 times the spatial resolution at which it is required to measure phase variations. In a typical high throughput application the spatial resolution is expected to be of the order 100 µm. Hence a detector plane fringe spacing of about 20 µm is required assuming unity magnification. Fringe fields with this geometry may be generated by introducing an angular shear between the reference and measurement wavefronts. For this purpose the arrangement shown in FIG. 6 may be used. Here the reference and object beams are passed through the adjacent facets of a small angle bi-prism 50 after reflection from the elements 7 and 8 of the test region and prior to recombination of the interferometer output. This prism arrangement is preferred because it is intrinsically insensitive to vibration and does not require that the simple planar geometry of the basic interferometer be modified. An angular shear $2\beta$ (rads) is thereby introduced between the beam where, $$\beta=(n-1)\alpha \quad (7)$$

$\alpha$=Inclination of the prism face ($\alpha$, $\beta$ are assumed small angles).

Figure 7:
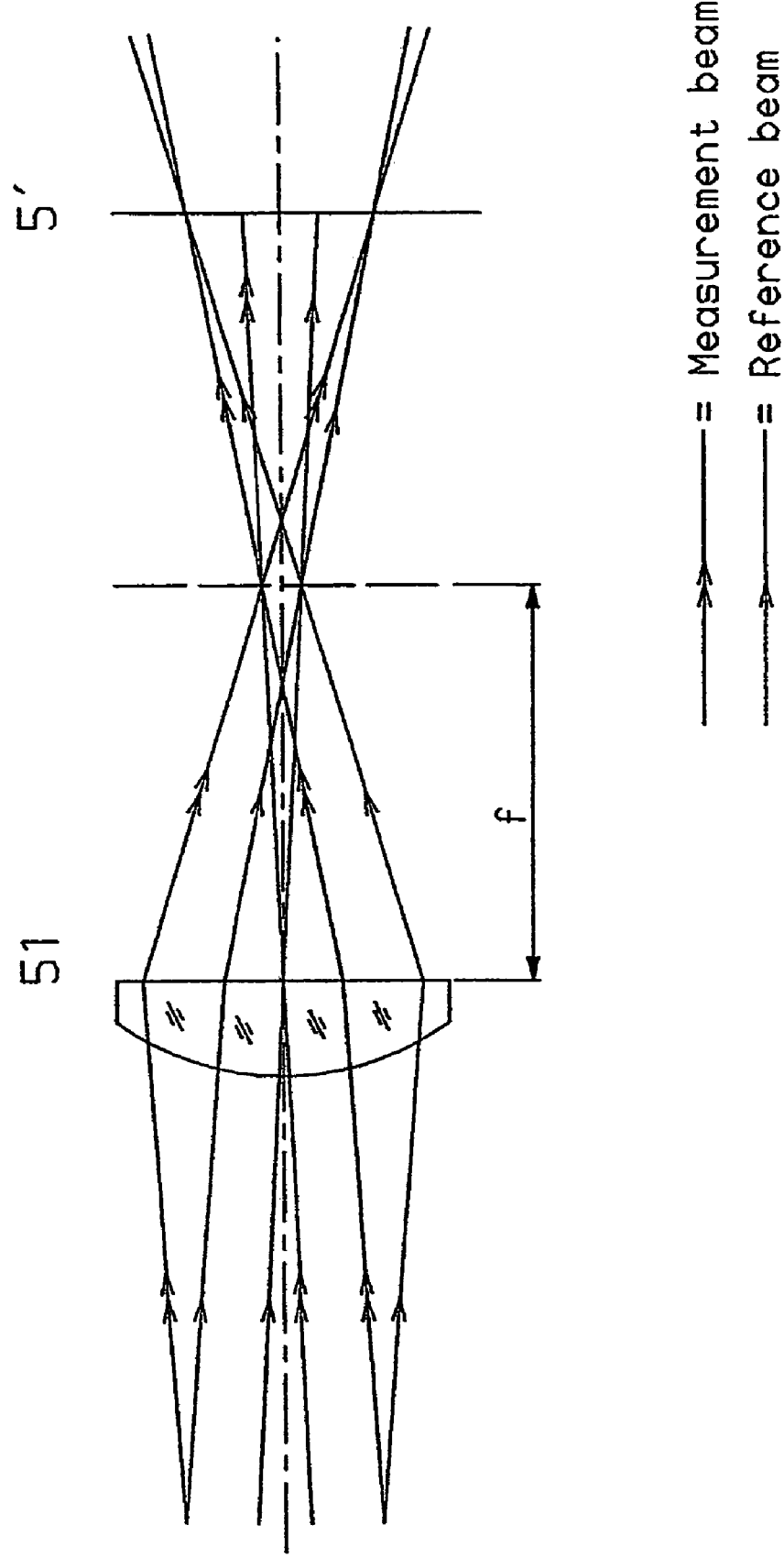
FIG. 7 is a diagram showing part of an interferometer in which a lens is used to superimpose the sheared interfering wavefronts in the plane of the detector array.

FIG. 7 shows how a lens 51 of focal length f in the output beam path following the combination point 15 shown in FIG. 3 may be used to superimpose the interfering beams in the plane of the pixelated detector 5'. The fringe spacing in this plane is given by s where, $$s = q\frac{\lambda}{2\beta} \quad (8)$$

where q is the ratio of the input beam diameter to that in the plane of the detector.

The path difference over which uniform fringe contrast needs to exist for total path differences is typically 0.2 mm i.e. the coherence length of the source should be of the order 1 to 10 mm for which stable, single mode operation is required to ensure high fringe stability.

In practice the combination of near diffraction limited plane wave illumination and high spatial and temporal coherence that results from the use of laser source causes the fringe and image planes to be non-localised. Consequently a fringe field is superimposed upon the measurement plane structure in any plane before or after the lens in which beam overlap occurs. The fringe spacing depends on q (equation 8) which is a function of this plane. The introduction of a lens results in a plane for which precise beam superposition occurs. The detector 5' shown in FIG. 7 is located in this plane.

There will now be described the Phase stepping method.

In this technique known optical path differences between the measurement and reference wavefront are introduced and the detector plane intensity distribution recorded for each change. If the complex amplitudes of the reference and measurement wavefronts at a point are respectively, $$U_r=u_r \exp(-i\phi_r) \quad (9)$$

$$U_m=u_m \exp(-i\phi_m) \quad (10)$$

and sequential plane steps of a quarter of a wavelength (equivalent to a phase step of $\Pi/2$) are applied the following equation is satisfied:

$$\phi_r - \phi_m = \tan^{-1}\left(\frac{I(x/2) - I(3\pi/2)}{I(0) - I(\pi)}\right) \quad (11)$$

In equation 11, I ($n\pi/2$) is the intensity recorded for the corresponding phase step (n=0, 1, 2, 3) and the required phase difference ($\phi_r - \theta_m$) is independent of the image intensity. The calculation defined by this equation is performed for each pixel in the array and a 2D phase image thereby generated.

Figure 8:
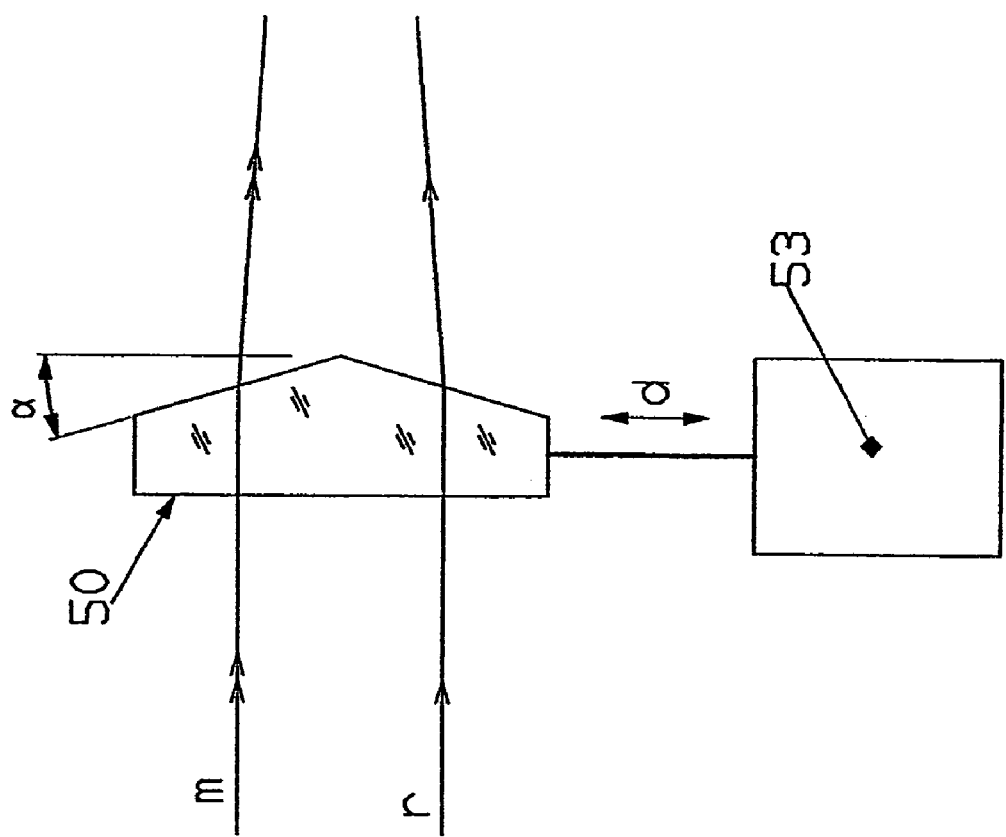
FIG. 8 is a diagram showing part of the interferometer in which a displacement is applied to a bi prism in order to generate a relative phase step between the interfering wavefronts.

Precise phase steps may be generated by translating the bi-prism 50 (FIG. 6) as shown in FIG. 8. Here an actuator 53 translates the prism 50 in its plane by a known distance d. This introduces a relative path difference, p between the reference and measurement wavefront where, $$p=2nd\alpha \quad (12)$$

and n=refractive index of the prism $\alpha$ must be selected such that the fringe spacing generated by the shear intrinsic to the arrangement can be resolved by the detector and the required path difference p compatible with the displacement range of the actuator. In practice the latter may consist of a piezo actuator with integral position transducer and a typical displacement range of 100 µm. For p of order 1 µm it is found that $\alpha \sim 10^{-2}$ rads for which the fringe spacing is nominally 30 µm (using equation 8 with q=1). This is compatible with what is required for the Fourier Transform method and hence the same basic system with the addition of a prism translation mechanism may be used for both phase measurement methods.

Figure 9:
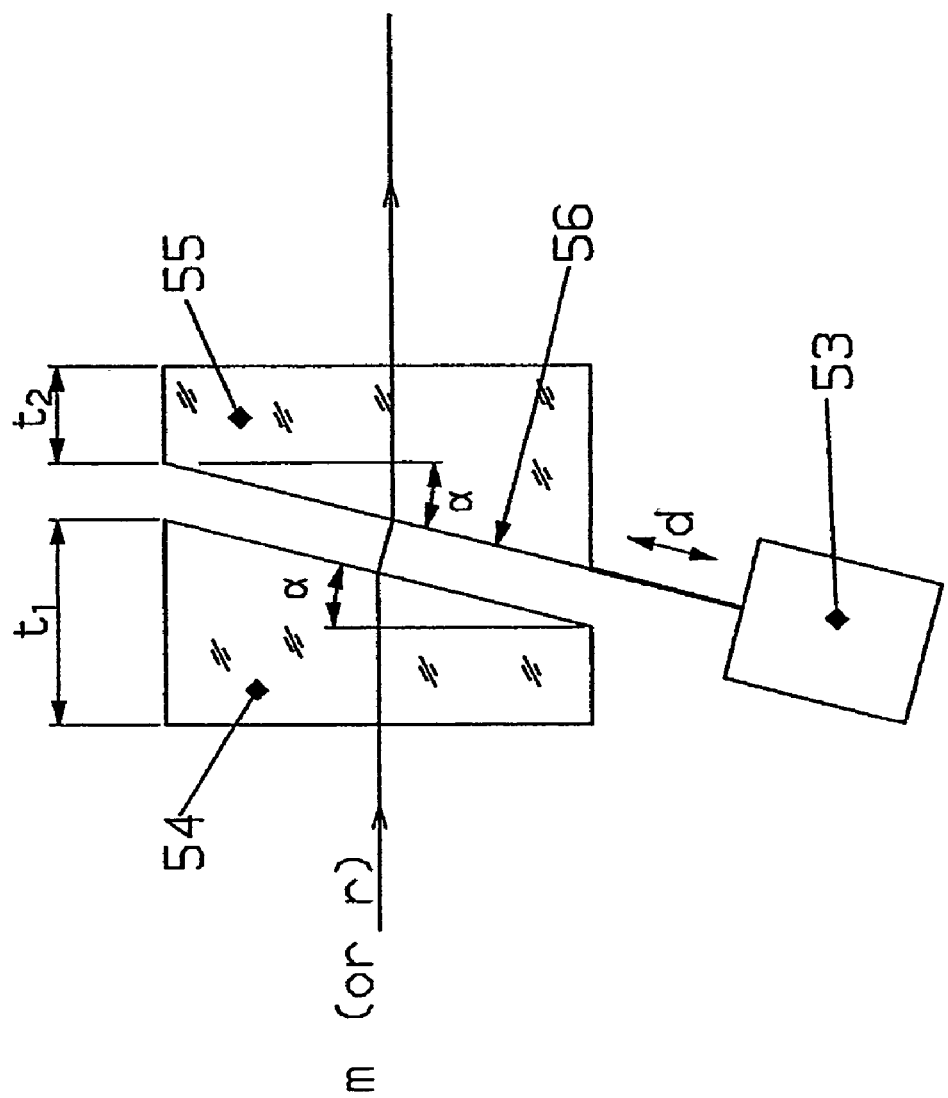
FIG. 9 is a diagram showing part of the interferometer in which a displacement is applied to single angle prism in order to generate a relative phase step between the interfering wavefronts.

An alternative method for introducing the phase shift without the introduction of an angular shear between the wavefronts is shown in FIG. 9. In this the beam which it is required shift in phase is passed through two matched prisms 54 and 55 having the same prism angle α. The phase shift is introduced by translating one of the prisms in a distance d relative to the other in a direction parallel to its inclined face.

In FIG. 9 the prism 55 is shown being translated in this way by the actuator 53. A path length difference ndα is thereby introduced without angular deviation of the beam. This is because the beam effectively sees a parallel sided optical flat of varying optical thickness n[(t1+t2)−dα)] where t1 and t2 are the thick and thin prism thickness respectively. This phase shift may be introduced relative to a zero phase difference by introducing a parallel faced block of the same refractive index and thickness (t1+t2) into the other beam. In such an arrangement coherence need only be maintained over a few wavelengths and for which a single mode laser is not required.

The basic illumination system discussed above may be adapted for different operational requirements as will now be described.

Figure 10:
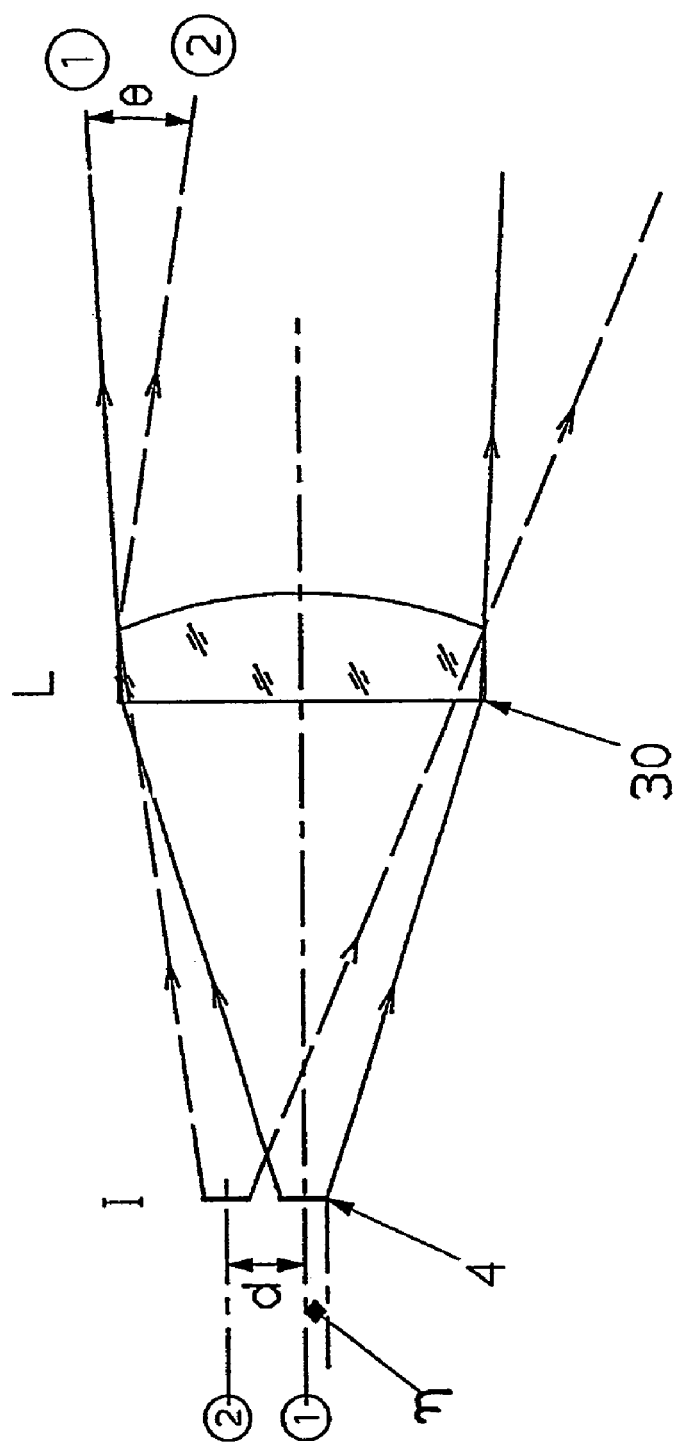
FIG. 10 is a diagram showing an optical configuration by which a translation of the source causes the direction of propagation of the collimated wavefront to rotate about the optical axis of the collimating lens.

For some applications it may be advantageous to be able to vary the angle of illumination over a small range in order to tune for optimum resonance. For this purpose the translation of the source 4 by a distance d from 1 to 2 in the focal plane of the collimating lens 30 as shown in FIG. 10 may be used. This results in the central axis of the collimated beam being rotated by an angle θ where θ=d/f. This therefore enables the angle of incidence to be varied without perturbation of the remainder of the opto-mechanical system. In a practical implementation the focal plane illumination source may consist of an optical fibre linked to a remote light source and attached to a displacement transducer.

Figure 11:
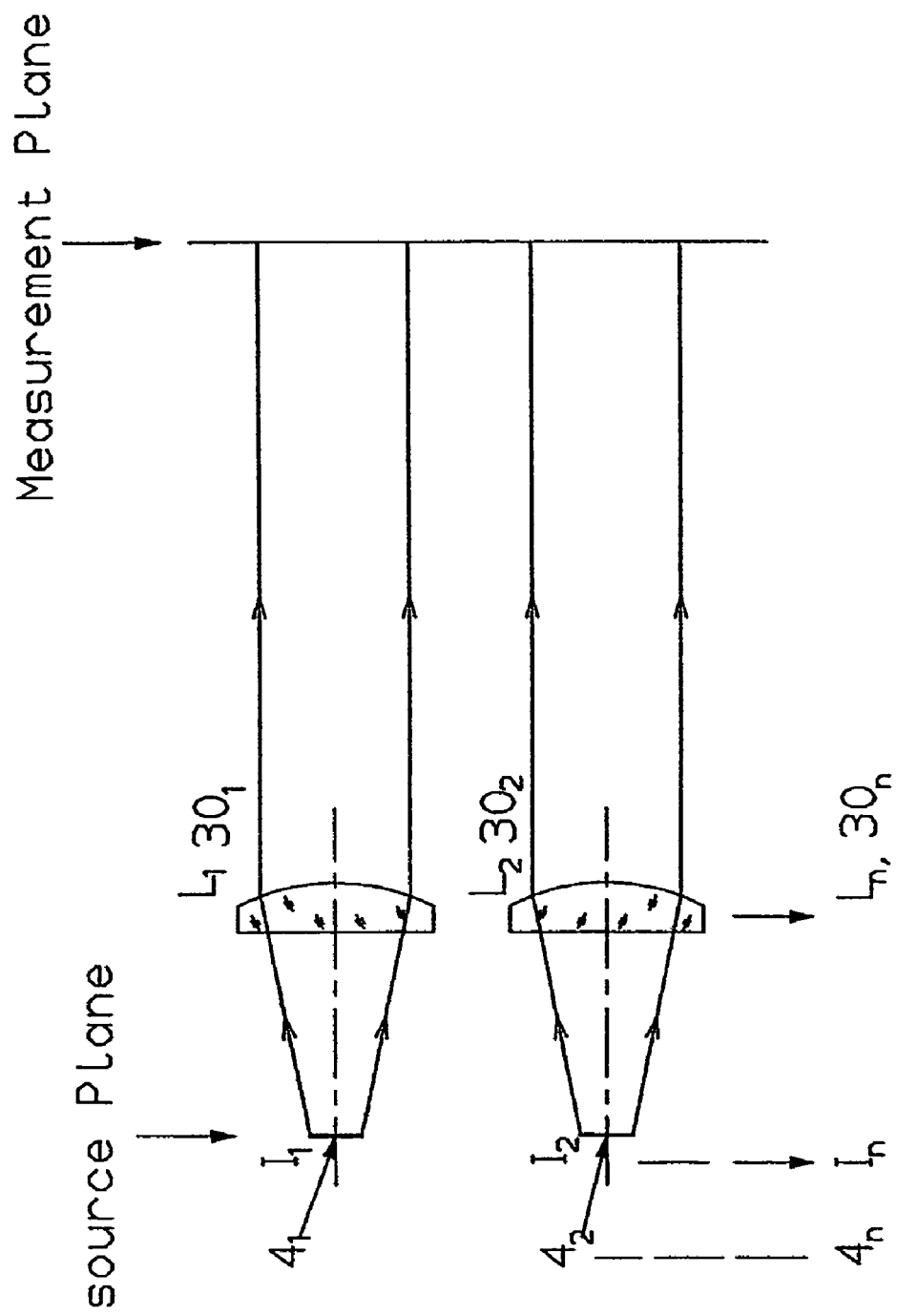
FIG. 11 is a diagram showing an array of individually collimated light sources.

FIG. 11 of the accompanying drawings shows a variant in which a plurality of similar optical illumination systems are provided with parallel optical axes. Thus whilst FIG. 5 shows one such system it will be appreciated that there can be an array of light sources 4, $4_1$, $4_2$, ... $4_n$, each of which have an associated lens, polariser and if necessary narrow band pass filter. Use of such an array of light sources enables an increased part of the measurement areas of the embodiments described to be utilised substantially increasing the amount of analysis which can be carried out by a single interferometer.

Figure 12:
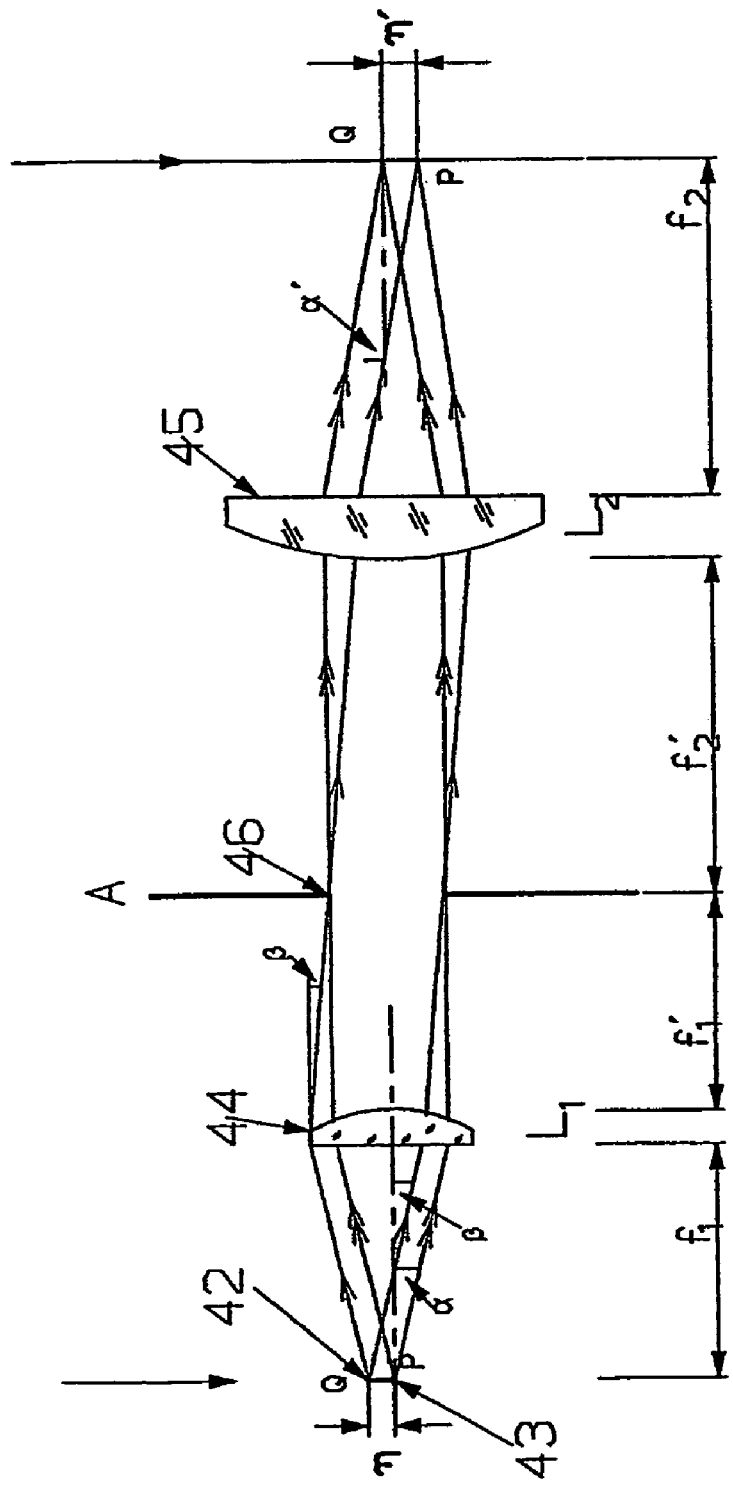
FIG. 12 is a diagram showing telecentric illumination optics based on an array of sources;.

Referring now to FIG. 12, this shows a twin lens telecentric system as an alternative to a lens array. The telecentric system results in an illumination beam consisting of a parallel pair of rays with covergence angle α' for the two sources 42 and 43. The two lenses 44 and 45 have $f_1$ and $f_2$ as their focal lengths and the two light sources 42 and 43 separated by a distance η are located in the focal plane of lens 44. The arrangement can be extended to multiple sources which may be any of the light sources already described. The system is constrained by the following two equations which follow from the Lagrange invariant:

$$\alpha' = \alpha \frac{f_1}{f_2} \quad (13)$$

$$\eta' = \eta \frac{f_2}{f_1} \quad (14)$$

This telecentric system is provided with a stop 46.

Figure 15:
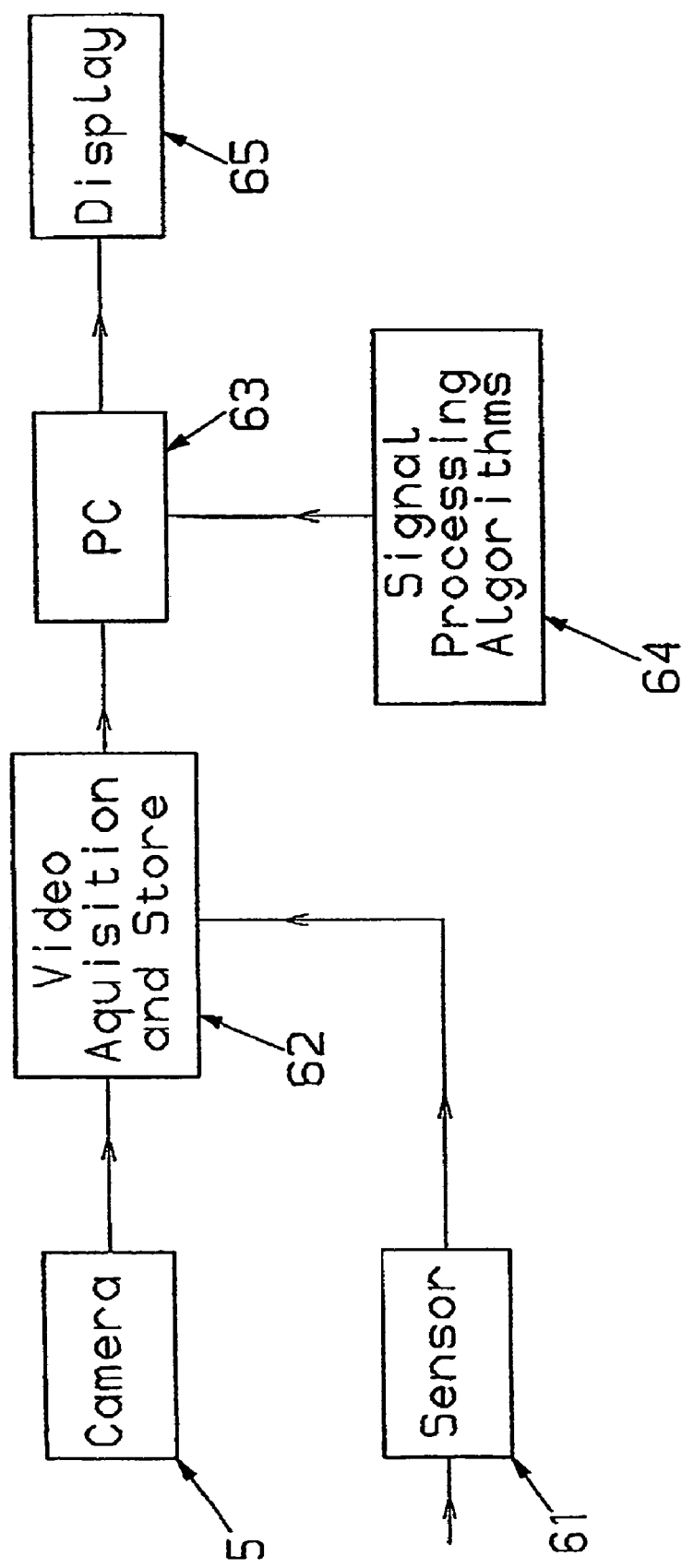
FIG. 15 is a block diagram showing a signal processing unit.

FIG. 15 shows the typical constituent elements of the signal processing unit 6 shown in FIG. 3. In operation a synchronisation pulse indicating, for example, the injection of binding molecules is delivered by the unit 61. There are many ways obvious to a person skilled in the art in which the apparatus can be alerted to the imminent presence of probe molecules. This triggers the acquisition and storage of the video data by a video frame grabber and store 62. A typical example of a frame grabber is that available on the market as "Coreco Imaging PC-DIG-LVDS" (TM). This data is processed by a digital processor 63 (PC, DSP etc . . . ) using algorithms 64. Data is displayed by 65 which may in practice be a VDU.

Figure 16:
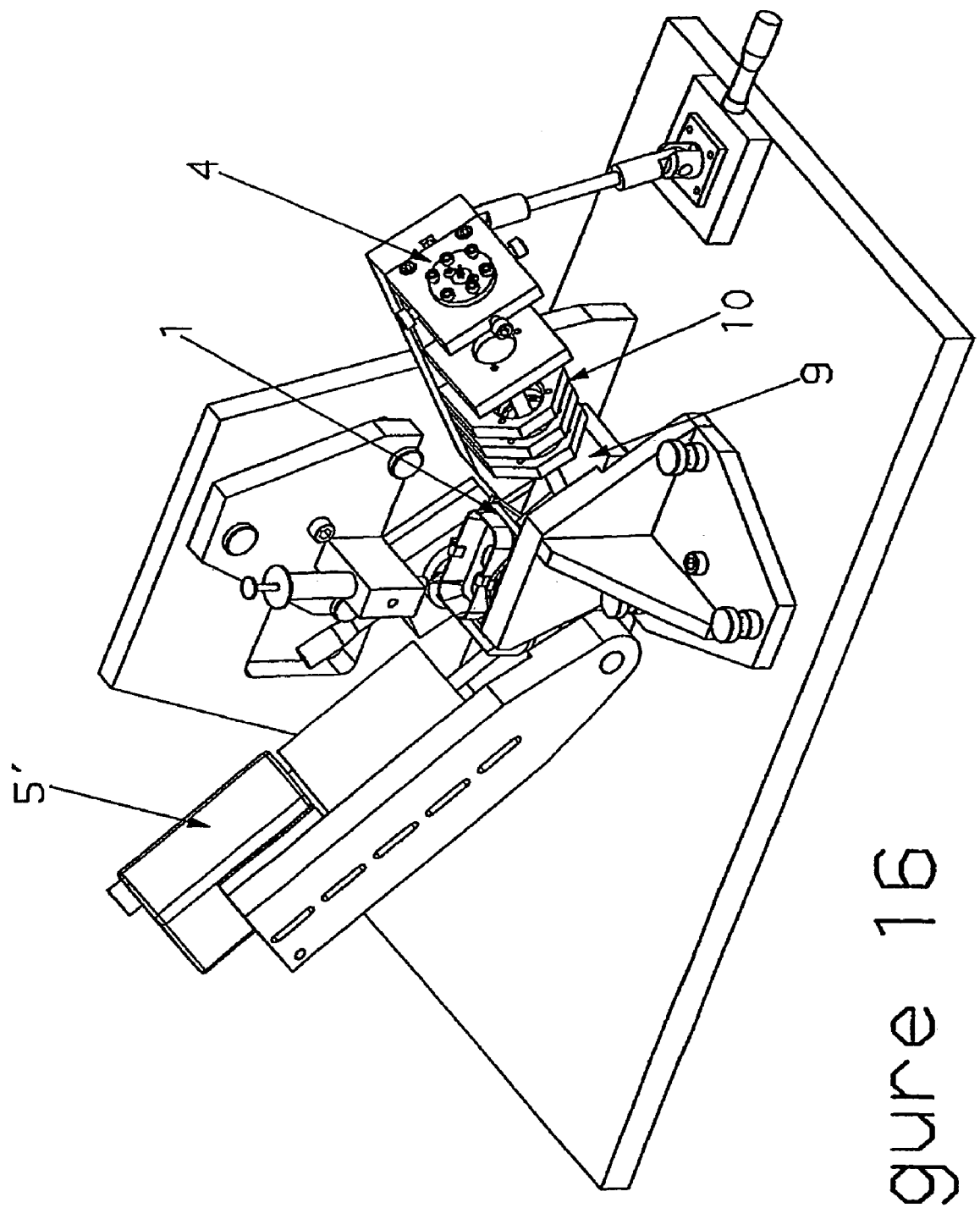
FIG. 16 is a perspective view of one practical embodiment.

FIG. 16 shows a typical practical configuration of the system with some of the elements shown in previous figures indicated.

It will be appreciated that the optical flat 2 and the metal film 3 (which may carry the chemical attachment layer 3') can be permanently adhered to the relevant face of the prism 1. However, in a preferred embodiment the optical flat 2 and film 3 are formed as a removable slide which can be suitably mounted so as to be tightly held against and index matched to the face of the prism 1. Thus after testing the slide can be removed and a freshly prepared slide introduced, thus increasing the rate of testing.

Figure 17:
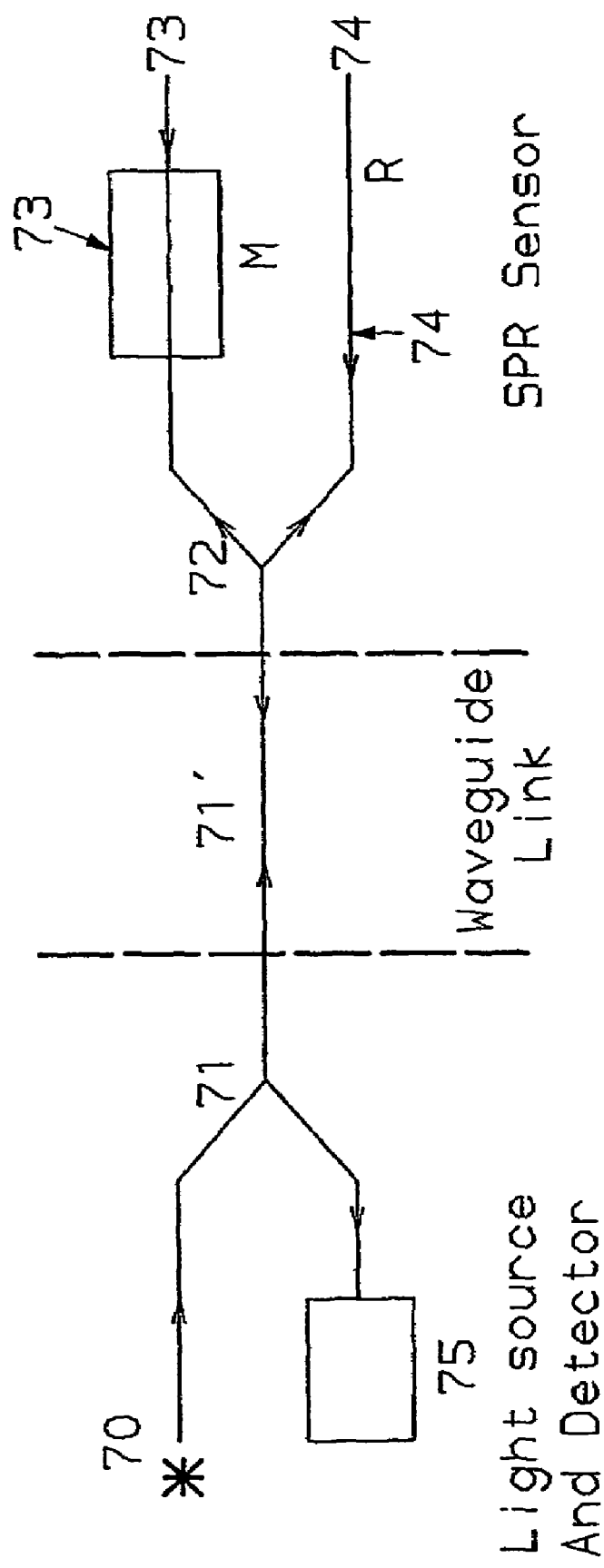
FIG. 17 is a diagram showing an implementation of the invention using waveguides.

FIG. 17 shows an equivalent waveguide configuration of the system. In this system light from a light source 70 is coupled via a bi-directional waveguide beam coupler 71 into a linkage waveguide 71' which is coupled into a second bi-directional waveguide coupler 72. The outputs from the latter couples light into the waveguide measurement arm 73 (M) and waveguide reference arm 74 (R) of the sensor. The measurement arm is configured to be resonant by modification of the waveguide geometry. The upper surface of the waveguide may, for example, be made planar and coated with gold of appropriate thickness. Light passing through the waveguides 73 and 74 is reflected from the respective waveguide end facets 73', 74' and interferes on recombination at the directional coupler 72. It is then coupled back via 71' and 71 to the detector 75 where the light field is detected and the phase shifts measured.

In practice the measurement and reference waveguide can be placed in very close proximity. Under these conditions non-resonant effects due to temperature changes, vibration, etc . . . are, to a very good approximation, common to both waveguides. The measured phase changes are therefore due primarily to surface plasmon resonance effects in the measurement channel.

In a preferred configuration the path difference between the reference and measurement channels is made greater than the coherence length of the light source. This enables the interference pattern to be reconstituted at a remote processing interferometer placed at the output of the system. For example, in such an arrangement the unit 75 in FIG. 17 would be replaced by a processing interferometer and detector. The introduction of this second interferometer enables the fringes to be optimally processed.

The following applications are listed to demonstrate particular potential uses of the interferometer. They do not exclude the possibility of applications for the interferometer that are not described here.

Figure 13:
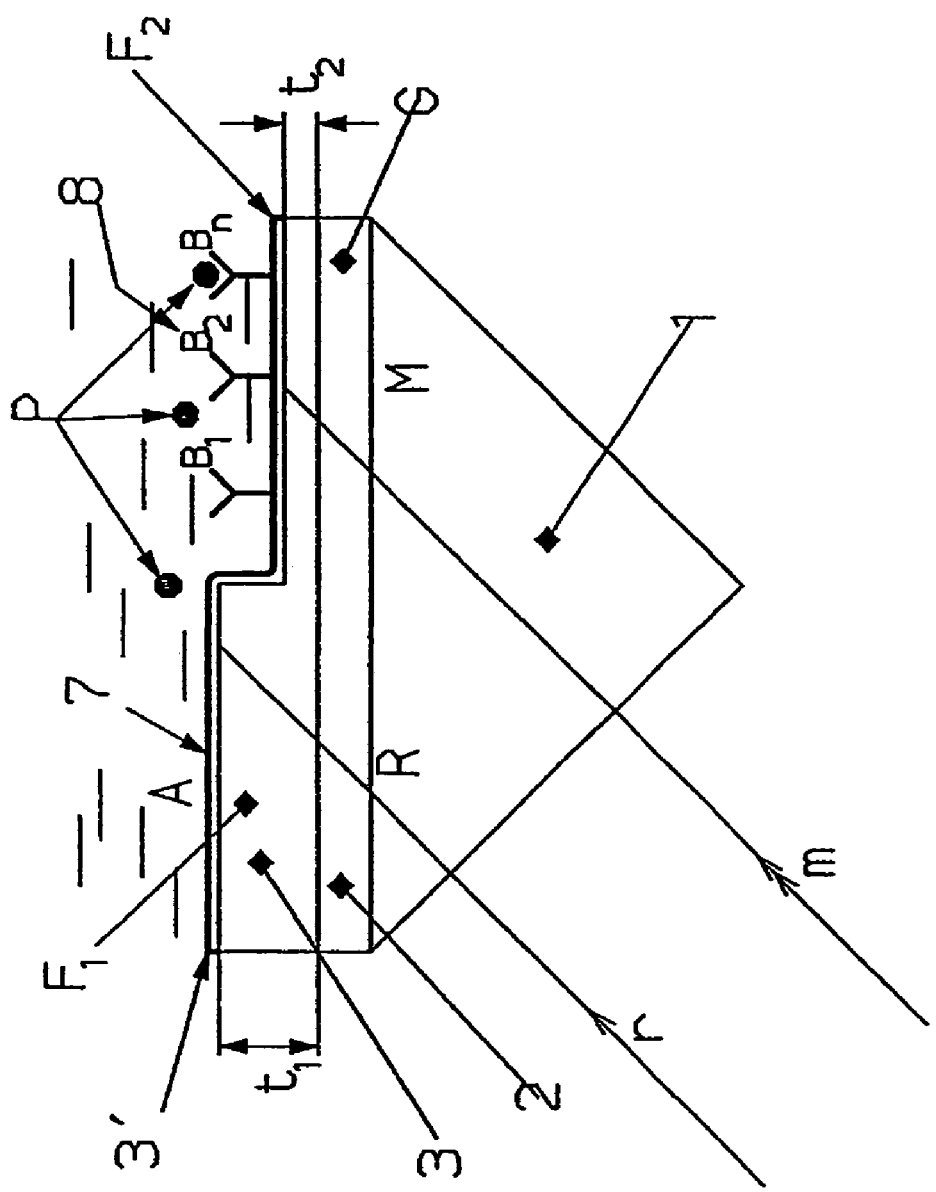
FIG. 13 is a diagram showing one arrangement of the reference and measurement surfaces in which the thickness of the coating in the reference region is such that it does not support resonance and that in the measurement region is at a resonant thickness. The diagram also shows a binding layer conformably coated on both the reference and measurement films.
Figure 14:
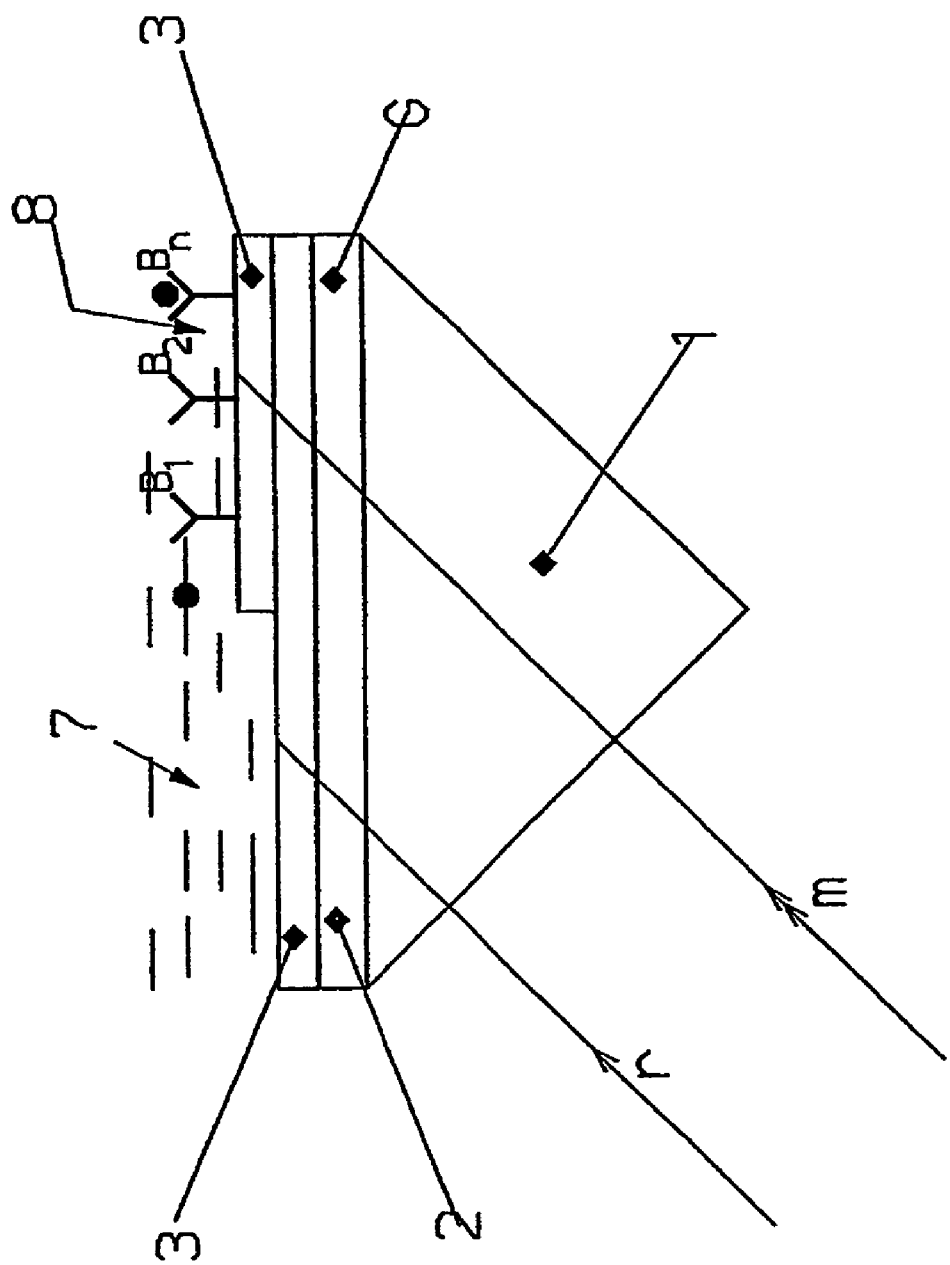
FIG. 14 is a diagram showing an alternative arrangement of the reference and measurement surfaces in which both have the same resonant coating thickness. The binding layer conformably coats the measurement surface only.

As mentioned a particularly important application is the detection of molecular binding and FIGS. 13 and 14 show configurations of the embodiment of FIGS. 3 and 4 for this purpose.

As has been discussed previously the substrate 2 is optically contacted with the prism 1 and coated with a thin metallic film 3 carrying a chemical attachment layer 3'. In the case of the arrangement shown in FIG. 13 the thickness of this metallic coating of the reference region 7 is such that it does not support resonance and that in the measurement region 8 is at resonant thickness. A second thin chemical attachment film 3' conformably coats the metallic film in the measurement area. Discrete binding sites $B_1$ to $B_n$, which may consist of probe molecules such as antibodies, or other molecules with specific affinities, are deposited on the chemical attachment film 3' in the measurement area 8. In a typical experiment the angle of incidence of the illumination is adjusted such that the composite surface 3, 3', $B_1$ to $B_n$ is at peak resonance with the incident light field in the presence of an analyte fluid which is passed over the binding sites B in a suitable conduit 50. The reference phase is recorded in this state and molecules P such as proteins are then introduced into the analyte and a change in phase at a binding site used to detect the molecular binding of P to B at that site.

Non-resonant phase changes common to the reference and measurement zones cancel out automatically in this configuration as a result of the latter being non-resonant. It will also be recognised that the conformed chemical attachment film 3' may extend over both regions.

In the arrangement shown in FIG. 14 the metallic film 3 is coated with a uniform resonant thickness so that both the reference zone 7 and measurement zone 8 are intrinsically resonant. The chemical attachment film 3 is however, applied only to the measurement zone. Under these conditions it will be seen that in the mode of operation described above resonant and non-resonant phase changes not associated with molecular binding that are common to both surfaces cancel out automatically.

Thus the interferometer may be used for monitoring the interactions between various types of molecules, where one of those molecules (hereafter referred to as the "probe" molecule) is immobilised to the surface of the array 3. In this manner, probe molecules are tested for their ability to bind other molecules—hereafter known as "target" molecules.

Probe molecules are localised at particular defined sites on the surface of the array. The entire array may consist of many separate probe sites ($B_1$ to $B_n$), containing identical or different probe molecules. Multiple similar or different molecules, built on or attached to each other, can also be used to detect binding of molecules in the sample.

In its experimental application, the surface carrying probe molecules may be exposed to a sample solution. Binding may occur between probe molecules immobilised on the array surface, and target molecules in the same solution. The interferometer described will enable the detection of binding events that occur between probe molecules localised on the array and target molecules in the solution.

The method and apparatus just described has a number of advantages over the prior art. In particular it allows many probe molecules to be studied simultaneously; it enables binding of a target molecule to be detected without the need for labelling the target molecule with another chemical such as a fluorescent, chemiluminescent or bioluminescent tag, or with radioactivity; and it enables binding between probe molecules and target molecules to be monitored in real time.

Detection of binding may allow a measurement of the quantity of target molecule present in the sample. It may also allow measurement of the kinetics and affinity of the interaction between the probe and the target molecules.

The embodiments described are also suitable for detecting many combinations of interactions between types of molecules that include but are not limited to: proteins, antibodies, nucleic acids (including DNA, RNA and derivatives thereof), other biological molecules (including but not limited to carbohydrates, lipids, vitamins, hormones, peptides) and chemicals (including but not limited to chemical therapeutic compounds and drugs).

In principle, the interferometer may detect interactions between any of these types of molecules as probe, and any of these types of molecules as target.

The target molecules may be present in a sample solution of which they are the only solute or component. The target molecules may also be present in a complex sample with many constituents in addition to the target molecules.

When the probe molecules are multiple different antibodies, and the target molecules are proteins for which the antibodies have certain affinities, and the same is a biological preparation, the amount of binding between probe molecules and target molecules detected by the interferometer can be used to determine the quantities of those proteins in the original sample.

Detecting levels of proteins in biological samples may be used to gain insight into gene function amongst other applications. Changes of protein levels that correspond to changes in the nature of the biological preparation, such as the onset of disease, can be used to reveal functional correlations between proteins, genes and biological phenomena such as disease, response to drugs (toxicology) and all the molecular and cellular processes of life.

Functional information about genes and proteins may be used to select genes and proteins as potential targets for the development of drugs to intervene in disease functions. Functional information about genes and proteins can also be used to understand and predict the activity of therapeutic drugs in affecting disease process, in causing toxicity, and in other pharmalogical and biological effects. Functional information about genes and proteins can also be used to gain understanding of the basic processes of life, in health and in disease. Information about the association between protein levels and different cellular or biological states can be used to generate diagnostic tests that determine the existence of that particular cellular or biological state—e.g. disease.

When used with the appropriate probe molecules, the interferometer described here can itself be used as a device for diagnosing disease, or monitoring other conditions in patients or in animals, such as pregnancy.

When the probe molecules are multiple different proteins, and the target molecules are proteins (or other molecules) for which the probe proteins may have affinity, and the sample is a preparation containing one or more proteins (or other molecules), the amount of binding between probe molecules and target molecules detected by the interferometer can be used to determine the degree of interaction between the probe molecule and the target molecules.

Information regarding the degree of interaction between probe proteins and target molecules can give insight into the function of proteins. Most proteins carry out their activities by binding to other molecules. Therefore testing the binding to molecules can give insight into their function in the cell or organism.

Information regarding the functions of proteins and genes can be used to understand the basis of cellular activities in health and disease. Understanding the functions of proteins in disease can identify potential targets for intervention with drug therapies, as well as allowing other applications, as described above.

When the probe molecules are multiple different chemicals or other molecules, and the target molecules are proteins, and the sample is a preparation containing one or more proteins, the amount of binding between probe molecules and target molecules detected by the interferometer can be used to determine the degree of interaction between the probe molecule and the target protein.

Information regarding the degree of interaction between probe molecules and target proteins can be used to identify which probe molecules bind with affinity to the target protein.

Molecules identified as binding to proteins may be useful as therapeutic compounds if the protein is involved in a particular disease.

When the probe molecules are multiple different proteins, and the target molecules are actual or potential therapeutics (including but not limited to chemical compounds, biochemical compounds, antibodies or proteins), and the sample is a preparation containing one or more therapeutics, the amount of binding between probe molecules and target molecules detected by the interferometer can be used to determine the degree of interaction between the probe proteins and the target therapeutics.

Information about the interaction between therapeutics and proteins can give insight into the function of the therapeutics, which can be used in the development of therapeutics. Depending on the identity of the probe proteins, this information may include but is not limited to information regarding the toxicity of the therapeutic, the pharmacological behaviour of the therapeutic, the metabolism, excretion, absorption of the therapeutic, as well as the mechanism of action of the therapeutic in affecting a disease state.

When used with the appropriate probe molecules, the interferometer described here can itself be used as a device for diagnosing disease, or determining other conditions in patients or in animals.

The device will be especially appropriate for making diagnoses when many factors are involved, or for carrying out multiple diagnostic tests on a single sample in one reaction by using many probe molecules as appropriate.

Any of the applications listed above may potentially be carried out using real time detection of results. This facility can enable several further uses of the interferometer.

For example, many biological testing approaches rely on recapitulating processes which naturally occur in a cellular environment by reconstitution in a biochemical assay. These assays typically depend on initiating a process under certain conditions, and then observing the results of carrying out that process.

The embodiments described herein, with appropriate probe molecules as described above, will enable complex reactions to be observed as they progress in time by determining the levels of large numbers of different target molecules as they change through the course of a reaction. This can be particularly useful for biological reactions and pathways where many molecular effects are executed in particular sequences.

Monitoring this type of in vitro reaction can be useful in conducting basic research into the mechanisms of life in health and disease, as well as carrying out specific assays to understand disease processes and other biological processes relevant to development of therapeutics and diagnostics.

Additionally monitoring this type of in vitro reaction can enable real time feedback control mechanisms, where the constituents of the reaction vessel are adjusted and controlled automatically, according to information received from the interferometer device.

Many experimental and biological procedures rely on observing and controlling the growth and behaviour of cells, organs, tissues or micro-organisms in experimental vessels. The interferometer embodiment of the invention described here, with appropriate probe molecules as described above, will enable monitoring of the components of the medium in which such organic materials are grown in bioreactors.

Monitoring bioreactors can enable real time feedback control mechanisms, where the constituents of the reaction vessel are adjusted and controlled automatically, according to information received from the interferometer device.

When used with the appropriate probe molecules, a device based on the interferometer can be used to monitor the condition of patients in real time. The device may be especially useful in situations that require measurement of multiple different indications at the same time.

When used with the appropriate probe molecules, a device based on the interferometer can be used to monitor the presence and the levels of components and contaminants in foods and other substances. This has applications both for process control as well as quality assessment of products.

When used with the appropriate probe molecules, a device based on the interferometer can be used for the detection and measurement of substances in water, for example in re-processing plants and reservoirs.

Real time detection of binding between modules may be used to analyse the kinetics of the interaction between those molecules.

When used in an experiment with dynamically changing conditions, real time detection of binding between molecules may be used to analyse the affinity of the interaction between those molecules.

REFERENCES (1) Chemical and Bio chemical sensing with optical fibres and waveguides. G Boisde and Alan Harmer, 1996 Artech House Inc, Chapter 8 pp 222–224.
(2) Ariel G Notcovich et al, 2000, Applied Physics Letters, Volume 76, Number 13 pp 1665–1667.
(3) Bryce P Nelson, Annal. Chem, 1999, 71, 3928–3934.
(4) Jennifer M Brockman et al, Annu.Rev.Phys.Chem 2000. 51 pp 41–63.
(5) Takeda et al, J.Opt.Soc.Am. Vol 72, No 1, January 1982, 156–159.

The invention claimed is:

1. An interferometer comprising:
   an optical body adapted in operation to mount a measurement area comprising a film which is capable of acting as a two dimensional environment for surface plasmons and an adjacent reference area;
   an optical beam generation source for irradiating the reference and measurement areas with radiation capable of generating surface plasmon resonance;
   optical unit for combining radiation reflected from the reference and measurement areas, and a pixelated detector for generating data representing two dimensional images of the combined radiation beams.

2. An interferometer according to claim 1 wherein the optical body comprises a prism of which at least a part face provides, with the film, the respective measurement and reference areas.

3. An interferometer according to claim 1, wherein the optical body comprises a pair of prisms, at least a part of one face of one prism providing with the film a measurement area, and at least a part of one face of the other prism providing with the film a reference area.

4. An interferometer according to claim 1 wherein the optical beam generation source comprises a source of polarised light, and a parallel faced optical flat is located in the path of the optical axis of the polarised light source so as to split the light into a reference beam incident in use on the reference area and a measurement beam incident in use on the measurement area.

5. An interferometer according to claim 4, wherein said optical flat lies in the path of the light reflected from the respective reference and measurement areas so as to combine the light reflected from these areas.

6. A interferometer according to claim 4, wherein the light source is adapted to generate light plane polarised to the plane of incidence of the light to the reference and measurement surfaces.

7. An interferometer according to claim 4, wherein the light source comprises an optical fibre which can be coupled to a remote light source.

8. An interferometer according to claim 5 in which the optical body which comprises the two dimensional environment for surface plasmons and the reference and measurement beam separation and re-combination means form a single monolithic unit.

9. An interferometer according to claim 4, in which the reference and measurement beams pass through an additional optical element before recombination, said element being designed to introduce an angular shear between the said beams.

10. An interferometer according to claim 4, in which the reference and measurement beams pass through an additional optical element before recombination said element being designed to introduce a spatially uniform phase difference between the said beams.

11. An interferometer in accordance with claim 9 in which the said optical element or a component thereof may be moved so as to introduce a variable relative phase difference between the reference and measurement beams.

12. An interferometer in accordance with claim 9 in which the said optical element consists of a bi-prism.

13. An interferometer in accordance with claim 10 in which the said optical element consists of two optical wedges of the same angle so configured to form an optical flat of variable thickness when one prism is translated relative to the other.

14. An interferometer according to claim 1 in combination with a slide carrying said film.

15. An interferometer according to claim 14 in which the reference area on said slide is coated such that it cannot support surface plasmons.

16. An interferometer according to claim 14 in which both the reference and measurement area on said slide can support surface plasmons.

17. An interferometer according to claim 15 in which both the reference and measurement areas on said slide are conformably coated with a chemical attachment film.

18. An interferometer according to claim 15 in which only the measurement area on said slide is conformably coated with a chemical attachment film.

19. An interferometer in accordance with claim 1 comprising a waveguide for coupling the light source via respective waveguides having independent paths to the respective measurement and reference areas.

20. An interferometer according to claim 19 wherein the path lengths of the respective waveguides have a path length difference which is greater than the coherence length of the source.

21. An interferometer in accordance with claim 20, including a second interferometer adapted to measure phase difference in said areas.

22. A method of interferometrically detecting variations in surface plasmon resonance forming a measurement area comprising a film which is capable of acting as a two dimensional environment for surface plasmon resonance, providing a reference area, which is not capable of supporting surface plasmon resonance, providing at least the measurement area with probe molecule ligands, irradiating the reference and measurement areas with radiation capable of generating surface plasmon resonance, passing an analyte past the measurement and reference areas, combining radiation reflected from the reference and measurement areas, and utilising pixellated detection means to generate two dimensional images of the combined radiation beams.

* * * * *